United States Patent [19]

Johnson et al.

[11] Patent Number: 5,430,047
[45] Date of Patent: Jul. 4, 1995

[54] NEUROTENSIN ANTAGONISTS

[75] Inventors: Stephen J. Johnson; Suzanne R. Kesten; Lawrence D. Wise; David J. Wustrow, all of Ann Arbor, Mich.

[73] Assignee: Warner-Lambert Company, Morris Plains, N.J.

[21] Appl. No.: 224,613

[22] Filed: Apr. 7, 1994

[51] Int. Cl.⁶ .............. C07D 257/04; C07C 65/32; C07C 65/40; A61K 31/19; A61K 31/41
[52] U.S. Cl. .............................. 514/381; 514/568; 548/253; 562/459; 562/463
[58] Field of Search .............. 548/253; 514/381; 562/459, 463

Primary Examiner—David B. Springer
Attorney, Agent, or Firm—Francis J. Tinney

[57] ABSTRACT

Neurotensin antagonists are described, as well as methods for the preparation and pharmaceutical composition of same, which are useful as central nervous system agents and are particularly useful as antipsychotic agents and as agents to treat Parkinson's disease and gastrointestinal disorders.

6 Claims, No Drawings

NEUROTENSIN ANTAGONISTS

BACKGROUND OF THE INVENTION

The present invention relates to novel neurotensin antagonists useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are antipsychotic agents for treating psychoses such as schizophrenia and are also useful as agents to treat Parkinson's Disease and gastrointestinal (GI) disorders.

Neurotensin (NT), is an endogenous neuropeptide distributed throughout the central nervous system (CNS) (Uhl G. I. R., et al., *Prc. Natl. Acad. Sci. USA*, 74:4059–4063 (1977)) and gastrointestinal (GI) tract (Carraway R., Kitabgi P., Leeman S. E., *J. Biol. Chem.*, 253:7996 (1978)). While the physiological role of neurotensin is not precisely understood it appears to be a regulatory hormone in several systems both in the periphery as well as the central nervous system.

Neurotensin appears to be involved in the etiology of schizophrenia. In the central nervous system it appears to be a regulator of dopamine neurotransmission (Kalivas P., *Brain Research Reviews*, 18:75–113 (1993) and references cited therein). Neurotensin has been shown to increase both dopamine metabolism and the content of dopamine in the rat brain (Faggin B. M., et al., *J. Pharm. Exp. Ther.*, 252:817–825 (1990)). Electrophysiological studies have shown that neurotensin increases firing of dopamine neurons (Shi W.X., Bunney B. S., *Brain Res.*, 543:315–321 (1991)). In addition, neurotensin immunoreactive axons form synaptic specializations on dopamine perikarya and dendrites (Woulfe J., Beauder A., *Brain Res.*, 479:402–406 (1989)). Expression of the gene encoding for proneurotensin, the metabolic precursor to neurotensin, appears to be regulated by certain antipsychotic drugs (Merchant K., Dobie D. J., Dorsa D.M., *Ann. N.Y. Acad. Sci.*, 668:54–69 (1992)). Clinical evidence for the involvement of neurotensin in the etiology of schizophrenia is suggested by the elevation of neurotensin levels found in the study of postmortem brain tissue of schizophrenics (Nemeroff C. B., et al., *Science*, 221:972–975 (1983) and references cited therein).. In addition, neurotensin has been suggested to be involved in the etiology of Parkinson's Disease (Chinaglia, G., et al., *Neuroscience*, 39:351–360 (1990)).

Neurotensin has also been shown to have effects in the GI tract including inhibition of gastric acid secretion and gastric emptying (Blackburn, A. M., *Lancet*, 1:987–989 (1980)), as well as pancreatic secretion (Sakamoto, T., et al., *Surgery*, 96:146–153 (1984)). Thus antagonists at the neurotensin receptor may be expected to have beneficial effects on various GI disorders.

To date, most peptide analogs of neurotensin and NT 8-13 (the minimum active fragment of neurotensin) have acted as agonists. Apparent exceptions to this are D-Trp[11]NT and Tyr(Me)[11]NT which have been shown in some assays to have weak antagonist activity (Rioux F.R., et al., *Eur. J. Pharmacol.*, 66:373–379 (1980)). Recently, $Asp^{13}$-$NT^{8-13}$ and $Asp^{12}$-$NT^{8-13}$ have been shown to antagonize histamine release from isolated mast cells (Miller L.A., Cochrane D. E., Carraway R.E., Feldberg R.S., *Agents Actions*, 38:1–7 (1993)).

Nonpeptidic neurotensin antagonists have also been described. European Published Patent Application EP-477049-A discloses 3-amido pyrazoles of formula (I) and (I') and their salts with acids or bases, and their enantiomers.

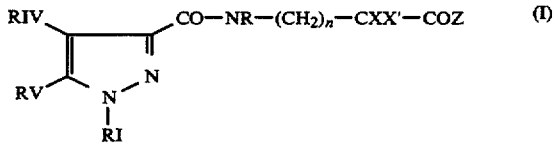

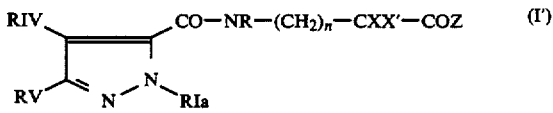

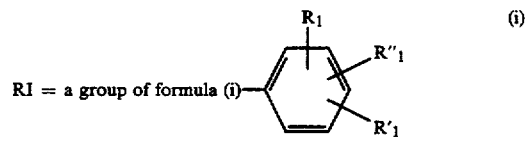

or carboxyalkyl; alkoxycarbonylalkyl (alkyl has $C_{1-4}$); $C_{3-6}$ cycloalkyl; tetrahydronaphthyl; pyridyl; naphthyl; or benzyl substituted by $R_1$, $R'_1$, and $R''_1$; cinnamyl optionally substituted on the phenyl ring by halogen, OH, or $C_{1-4}$ alkoxy; quinolyl or isoquinolyl, optionally substituted by $R_1$, $R_1'$, and $R_1''$; 2-benzothiazolyl; quinoxalinyl dione; 1-phthalazinyl; benzothiadiazolyl; or methylene substituted by a 5- or 6-membered heterocyclic group; $R_1$, $R'_1$, $R''_1$ =H, halogen, OH, $C_{1-4}$ alkyl, $C_{1-4}$ alkoxy, $CF_3$, $CF_3O$, $NO_2$, carboxy, or $NH_2$; RIa =benzyl substituted by $R_1$, $R_1'$, and $R_1''$; R =H or $C_{1-4}$ alkyl; n =0, 1, 2, or 3; either X =H and X'=H, $C_{1-6}$ alkyl, aryl, $C_{1-4}$ aminoalkyl, $C_{1-4}$ hydroxyalkyl, $C_{1-4}$ carboxyalkyl; acetamido ($C_{1-4}$) alkyl cysteine, guanidino ($C_{1-4}$) alkyl, nitroguanidino ($C_{1-4}$) alkyl, $C_{3-7}$ cycloalkyl, aralkyl (alkyl has $C_{1-4}$, aryl may be substituted by halogen, OH, or $C_{1-3}$ alkyl), or hetero(C-1-4)alkyl (heteroaryl is imidazolyl or indolyl optionally substituted by $C_{1-4}$ alkyl, OH, or $C_{1-4}$ alkoxy); or when n =0, X =H and X' and N—R together form an optionally OH-substituted ring of formula (ii)–(iv) or an indolyl, perhydroindole, or 4,5, 6, 7-tetrahydrothieno[2,3-c]-6-pyridyl ring;

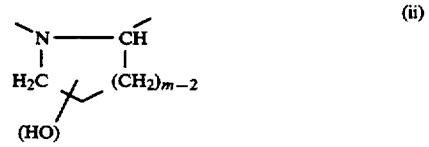

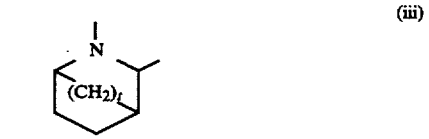

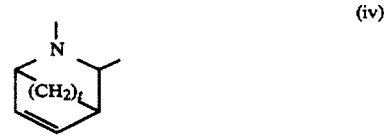

m=2–4;

t=1 or 2;

or X and X'=independently $C_{1-4}$ alkyl, $C_{3-6}$ cycloalkyl, or phenyl; or X and X' together form a $C_{2-12}$ cycloalkyl optionally substituted by $C_{1-3}$ alkyl; or X, X' and the C atom to which they are attached form an adamantyl group (which may be substituted by one or two methyl, or by one OH, $C_{1-3}$ alkoxy, or halogen), 1-aza adamantyl, quinuclidinyl, 4-piperidinyl (optionally N-substituted by benzyl), 2,2, 6, 6,-tetramethyl piperidinyl, tetrahydronaphthyl, 4-tetrahydropyranyl, 4-tetrahydrothiopyranyl, 2,3-dihydro-(4H)-4-benzo(thio)pyranyl, a group of formula (a), this group being attached to —NR— and to —COZ by a C atom of one or other rings; a group of formula (b) this group being attached to —NR— and to —COZ by a C atom on either of the rings (the rings of groups (a) and (b) optionally being substituted by one or two $C_{1-4}$ alkyl groups, and the amino acid not being alpha to W when W is O); 2-bicyclo [2,2,1]hepten-5-yl; 8-oxa-3-bicyclo[3,2,1]oct-6-en3-yl; or 8-oxa-3-bicyclo(3.2.1)octan-3-yl;

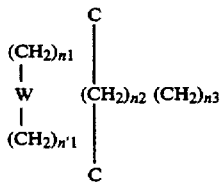

(a)

$n_1$=0 or 1;
$n'_1$=1 or 2;
$n_2$=1;
$n_3$=2 or 3;
W=C or O;

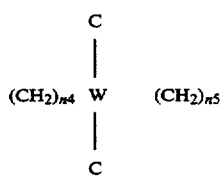

(b)

$n_4$=2, 3, or 4;
$n_5$=2 or 3;
W=C or O;

or X=H and X'=adamantyl (optional substituted as above ), 1-aza-adamantyl or a group of formula (a) or (b), the bond between the rings and the carbon carrying COZ and NR not being alpha to W when W is O; Z=OH, $C_{1-6}$ alkoxy, O substituted by a protecting group for carboxylic acids ( e. g., t-butyl or optionally substituted benzyl), amino or an N atom substituted by carboxy-$C_{1-6}$ alkyl; provided that if Z is the substituted N atom and if n=0, then when X=H, X' is not $(CH_2)_x$—COQ (x=1 or 2, Q=OH or free or substituted amino); RIV=H, halogen, or $C_{1-6}$ alkyl; RV=group of formula (v) naphthyl (optionally substituted by $C_{1-4}$ alkyl), pyridyl, or styryl (optionally substituted by $C_{1-4}$ alkyl);

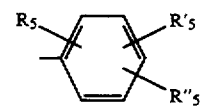

(v)

$R_5$, $R'_5$, and $R''_5$=H, halogen, $C_{1-4}$ alkyl, OH, $C_{1-4}$ alkoxy, $NO_2$, $CF_3$, $CF_3O$, CN, $NH_2$, carboxy, carboxy $(C_{1-4})$alkyl, or Ph; or RIV and RV together form a group (vi)

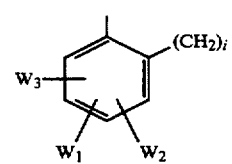

(vi)

where Ph substitutes the pyrazole group in position 5 and the group $(CH_2)i$, in which i is 1–3, substitutes the pyrazole in position 4; $W_1$, $W_2$, and $W_3$=H, halogen, or OH.

Gulley D., et al., *Proc. Natl. Acad. Sci USA.*, 90:65–69 (1993) disclose SR 48692, as a nonpeptide neurotensin receptor antagonist.

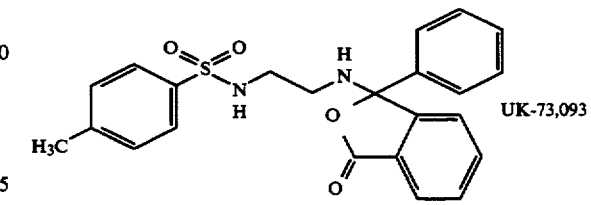

SR 48692

Snider R. M., et al., *Biorg. Med. Chem. Lett.*, 1535–1540 (1992) disclose UK-73,093, as a nonpeptide neurotensin receptor antagonist.

UK-73,093

A series of substituted quinazolines of the formula

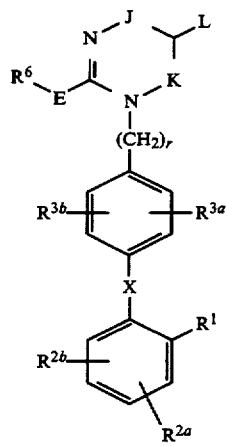

are disclosed in U.S. Pat. No. 5,204,354 as neurotensin antagonists useful in the treatment of central nervous system disorders.

The compounds disclosed in the aforementioned references do not disclose or suggest the combination of structural variations of the compounds of the present invention. Thus, we have surprisingly and unexpectedly found the compounds of the present invention are neurotensin antagonists.

SUMMARY OF THE INVENTION

Accordingly, the present invention is a compound of Formula I

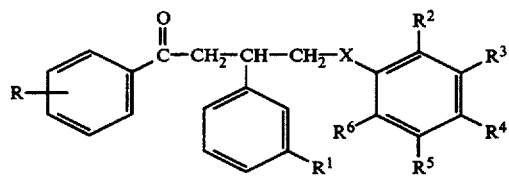

where X is

or —CH$_2$-;
R is hydrogen or halogen;
R$^1$ is —CO$_2$H or

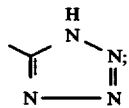

R$^2$, R$^3$, R$^4$, R$^5$, and R$^6$ are each the same or different and each is hydrogen, lower alkyl, lower alkoxy, or halogen;
or a pharmaceutically acceptable base addition salt thereof.

As neurotensin antagonists, the compounds of Formula I are useful as antipsychotic agents for treating psychoses such as schizophrenia. They are also useful as agents to treat Parkinson's Disease and GI disorders.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "lower alkoxy" is O-lower alkyl as defined above for lower alkyl.

"Halogen" is fluorine, chlorine, bromine, or iodine.

The compounds of Formula I are capable of further forming pharmaceutically acceptable base addition salts. All of these forms are within the scope of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *Journal of Pharmaceutical Science*, 66:1–19 (1977)).

The base addition salts of said acidic compounds are prepared by contacting the free acid form with a sufficient amount of the desired base to produce the salt in the conventional manner. The free base form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S (L) configuration. The present invention includes all enantiomeric and epimeric forms as well as the appropriate mixtures thereof.

A preferred embodiment is a compound of Formula I wherein R is 4-hydrogen or 4-halogen.

A more preferred embodiment is a compound of Formula I wherein R is 4-hydrogen, 4-chloro, or 4-fluoro.

Particularly valuable are:
3-[3-(4-Fluorophenyl )-1-[2-(4-fluorophenyl )-2-oxoethyl]-3-oxopropyl]-benzoic acid;
3-[3-(4-Chlorophenyl )-1-[2-(4-chlorophenyl )-2-oxoethyl]-3-oxopropyl]-benzoic acid;
3-[1-[2-(4-Chlorophenyl )-2-oxoethyl]-3-(2,5-dimethoxyphenyl)-3-oxopropyl]-benzoic acid;
3-[1-[2-(4-Chlorophenyl )-2-oxoethyl]-3-(2,4-dimethoxyphenyl)-3-oxopropyl]-benzoic acid;

3-[1-[2-(4-Chlorophenyl)-2-oxoethyl]-3-(3-methoxyphenyl)-3-oxopropyl]-benzoic acid;
3-[1-[2-(4-Chlorophenyl)-2-oxoethyl]-3-(2-methoxyphenyl)-3-oxopropyl]-benzoic acid;
3-[1-[2-(4-Chlorophenyl)-2-oxoethyl]-3-(2,6-dimethoxyphenyl) -3-oxopropyl]-benzoic acid;
3-[1-[2-(4-Fluorophenyl)-2-oxoethyl]-3-(2-methoxyphenyl)-3-oxopropyl]-benzoic acid;
3-[3-(4-Fluorophenyl)-3-oxo-1-(2-oxo-2-phenylethyl)-propyl]-benzoic acid;
3-[1-[2-(4-Fluorophenyl)-2-oxoethyl]-3-(4-methoxyphenyl)-3-oxopropyl]-benzoic acid;
3-[3-(2,5-Dimethoxyphenyl)-1-[2-(4-fluorophenyl)-2-oxoethyl]-3-oxopropyl]-benzoic acid;
3-[3-(2,6-Dimethoxyphenyl)-1-[2-(4-fluorophenyl)-2-oxoethyl]-3-oxopropyl]-benzoic acid;
3-[1-[2-(4-Chlorophenyl)-2-oxoethyl]-3-(4-methoxyphenyl)-3-oxopropyl]-benzoic acid;
3-[1-[2-(4-Chlorophenyl)-2-oxoethyl]-3-(4-fluorophenyl)-3-oxopropyl]-benzoic acid;
3-[1-[2-(4-Fluorophenyl)-2-oxoethyl]-3-oxo-3-p-tolylpropyl]-benzoic acid;
3-[1-[2-(4-Chlorophenyl)-2-oxoethyl]-3-oxo-3-p-tolylpropyl]-benzoic acid;
1,5-Bis-(4-fluorophenyl )-3-[3-(1H-tetrazol-5-yl)phenyl]-pentane-1,5-dione;
1,5-Bis-(4-chlorophenyl)-3-[3-(1H-tetrazol-5-yl)phenyl]-pentane-1,5-dione;
3-[1-[2-(4-Chlorophenyl)ethyl]-3-oxo-3-phenylpropyl]-benzoic acid;
3-[3-(4-Chlorophenyl)-1-[2-(4-chlorophenyl)-ethyl]-3-oxopropyl]-benzoic acid;
3-[1-[2-(4-Fluorophenyl)ethyl]-3-oxo-3-phenylpropyl]-benzoic acid;
3-[3-(4-Fluorophenyl)-1-[2-(4-fluorophenyl)-ethyl]-3-oxopropyl]-benzoic acid; and
3-[3-(4-Chlorophenyl)-3-oxo-1-[2-phenylethyl]-propyl]-benzoic acid;
or a pharmaceutically acceptable base addition salt thereof.

The compounds of Formula I are valuable neurotensin antagonists. The tests employed indicate that compounds of Formula I possess antipsychotic activity as well as activity useful in the treatment of Parkinson's Disease and GI disorders.

Thus, the compounds of Formula I were tested for their ability to inhibit [$^3$H] neurotensin binding in a receptor assay described by Mazella J., et al., *Journal of Biological Chemistry*, 263:144–149 (1988) and Kitabgi P., et al., *European Journal of Pharmacology*, 140:285–293 (1987). Compounds were tested as neurotensin antagonists using the functional assay described by Bunzou J. C., et al., *Biochem. J.*, 264:871–878 (1989) and Turner J., et al., *J. Pharm. Exp. Ther.*, 253:1049–1056 (1990). Thus, compounds were tested for their ability to inhibit neurotensin-induced calcium mobilization in HT29 cells.

The above test methods are incorporated herein by reference. The data in the table show the neurotensin receptor binding activity and calcium mobilization activity, of representative compounds of Formula I.

TABLE I

| | | Biological Activity of Compounds of Formula I | |
|---|---|---|---|
| Example | Compound | Inhibition of [$^3$H] Neurotensin Binding Ki (nM) | Inhibition of Neurotensin Induced Calcium Mobilization IC$_{50}$ µM |
| 1 | 3-[3-(4-Fluorophenyl)-1-[2-(4-fluorophenyl)-2-oxoethyl]-3-oxopropyl]-benzoic acid | 302 | |
| 2 | 3-[3-(4-Chlorophenyl)-1-[2-(4-chlorophenyl)-2-oxoethyl]-3-oxopropyl]-benzoic acid | 450 | |
| 3 | 3-[1-[2-(4-Chlorophenyl)-2-oxoethyl]-3-(2,5-dimethoxyphenyl)-3-oxopropyl]-benzoic acid | 18.7 | |
| 4 | 3-[1-[2-(4-Chlorophenyl)-2-oxoethyl]-3-(2,4-dimethoxyphenyl)-3-oxopropyl]-benzoic acid | 78 | |
| 5 | 3-[1-[2-(4-Chlorophenyl)-2-oxoethyl]-3-(3-methoxyphenyl)-3-oxopropyl]-benzoic acid | 136 | |
| 6 | 3-[1-[2-(4-Chlorophenyl)-2-oxoethyl]-3-(2-methoxyphenyl)-3-oxopropyl]-benzoic acid | 158 | |
| 7 | 3-[1-[2-(4-Chlorophenyl)-2-oxoethyl]-3-(2,6-dimethoxyphenyl)-3-oxopropyl]-benzoic acid | 161 | 2.2 |
| 8 | 3-[1-[2-(4-Fluorophenyl)-2-oxoethyl]-3-(2-methoxyphenyl)-3-oxopropyl]-benzoic acid | 213 | |
| 9 | 3-[3-(4-Fluorophenyl)-3-oxo-1-(2-oxo-2-phenylethyl) propyl]-benzoic acid | 223 | |
| 10 | 3-[1-[2-(4-Fluorophenyl)-2-oxoethyl]-3-(4-methoxyphenyl)-3-oxopropyl]-benzoic acid | 329 | |
| 11 | 3-[3-(2,5-Dimethoxyphenyl)-1-[2-(4-fluorophenyl)-2-oxoethyl]-3-oxopropyl]-benzoic acid | 331 | |
| 12 | 3-[3-(2,6-Dimethoxyphenyl)-1-[2-(4-fluorophenyl)-2-oxoethyl]-3-oxopropyl]-benzoic acid | 392 | |
| 13 | 3-[1-[2-(4-Chlorophenyl)-2-oxoethyl]-3-(4-methoxyphenyl)-3-oxopropyl]-benzoic acid | 426 | |
| 14 | 3-[1-[2-(4-Chlorophenyl)-2-oxoethyl]-3-(4-fluorophenyl)-3-oxopropyl]-benzoic acid | 440 | |
| 15 | 3-[1-[2-(4-Fluorophenyl)-2-oxoethyl]-3-oxo-3-p-tolylpropyl]-benzoic acid | 448 | |
| 16 | 3-[1-[2-(4-Chlorophenyl)-2-oxoethyl]-3-oxo-3-p-tolylpropyl]-benzoic acid | 579 | |
| 17 | 1,5-Bis-(4-fluorophenyl)-3-[3-(1H-tetrazol-5-yl)phenyl]-pentane-1,5-dione | 6316 | |
| 18 | 1,5-Bis-(4-chlorophenyl)-3-[3-(1H-tetrazol-5-yl)phenyl]-pentane-1,5-dione | 5896 | |
| 19 | 3-[1-[2-(4-Chlorophenyl)ethyl]-3-oxo-3-phenylpropyl]-benzoic acid | 17730 | |
| 20 | 3-[3-(4-Chlorophenyl)-1-[2-(4-chlorophenyl)ethyl]-3-oxopropyl]-benzoic acid | 6738 | |
| 21 | 3-[1-[2-(4-Fluorophenyl)ethyl]- | 29532 | |

TABLE I-continued
Biological Activity of Compounds of Formula I

| Example | Compound | Inhibition of [³H] Neurotensin Binding Ki (nM) | Inhibition of Neurotensin Induced Calcium Mobilization IC$_{50}$ µM |
|---|---|---|---|
| | 3-oxo-3-phenylpropyl]-benzoic acid | | |
| 22 | 3-[3-(4-Fluorophenyl)-1-[2-(4-fluorophenyl)ethyl]-3-oxopropyl]-benzoic acid | 3235 | |
| 23 | 3-[3-(4-Chlorophenyl)-3-oxo-1-[2-phenylethyl]propyl]-benzoic acid | 10378 | |

A compound of Formula Ia

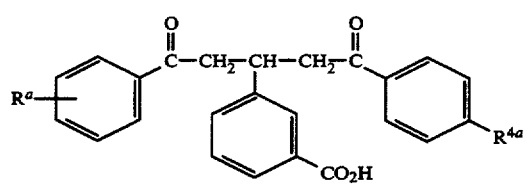

wherein $R^a$ or $R^{4a}$ are each either hydrogen, or the same halogen or a pharmaceutically acceptable base addition salt thereof is prepared by reacting 3-formylbenzoic acid with a compound of Formula II

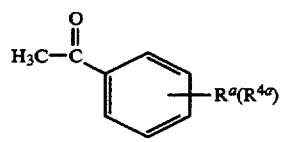

wherein $R^a$ ($R^{4a}$) is as defined above with a base such as, for example, sodium hydroxide and the like and an alcohol and water such as, for example, ethanol and water and the like to afford a compound of Formula Ia.

Preferably, a compound of Formula Ia is obtained by reaction with sodium hydroxide in ethanol and water.

A compound of Formula Ib

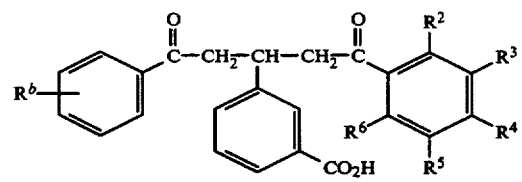

wherein $R^b$ is hydrogen, chloro, or fluoro; and $R^2$, $R^3$, $R^4$, $R^5$, and $R^6$ are each the same or different and each is
 hydrogen,
 lower alkyl,
 lower alkoxy, or
 halogen,
or a pharmaceutically acceptable base addition salt thereof is prepared by reacting 3-formylbenzoic acid with a compound of Formula IIa

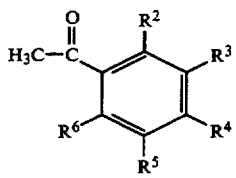

wherein $R^2$, $R^3$, $R^4$, $R^5$, and $R^6$ are as defined above with a base such as, for example, sodium hydroxide and the like in a solvent such as, for example, an alcohol such as aqueous ethanol and the like followed by subsequent treatment with an acid such as, for example, sulfuric acid in a solvent such as, for example, an alcohol such as methanol and the like to afford a compound of Formula III

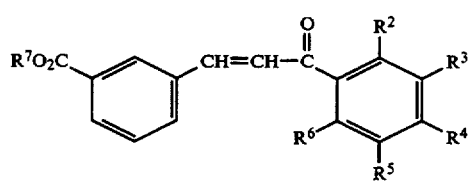

wherein $R^7$ is lower alkyl and $R^2$, $R^3$, $R^4$, $R^5$, and $R^6$ are as defined above.

Preferably, the reaction is carried out with sodium hydroxide and aqueous ethanol and subsequent treatment with sulfuric acid and methanol. Treatment of a compound of Formula III with a compound of Formula IV

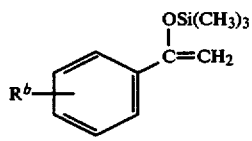

wherein $R^b$ is as defined above in the presence of trityl pentachlorostannate (TrSnCl$_5$) in a solvent such as, for example, dichloromethane and the like to afford a compound of Formula V

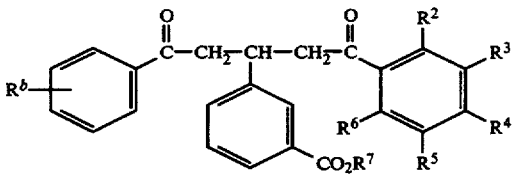

wherein $R^b$, $R^2$, $R^3$, $R^4$, $R^5$, $R^6$, and $R^7$ are as defined above. Preferably, the reaction is carried out with TrSnCl$_5$ in dichloromethane. Treatment of a compound of Formula V with a base such as, for example, potassium trimethyl silanolate and the like in a solvent such as, for example, diethyl ether and the like affords a compound of Formula Ib. Preferably, the reaction is carried out with potassium trimethyl silanolate and diethyl ether.

A compound of Formula Ic

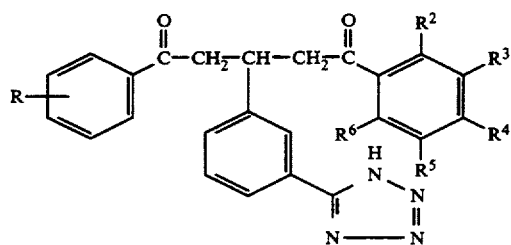

wherein R is hydrogen or halogen and $R^2$, $R^3$, $R^4$, $R^5$, and $R^6$ are as defined above, or a pharmaceutically acceptable base addition salt thereof is prepared by reacting a compound of Formula IIb

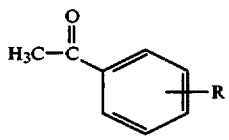

wherein R is defined above with $(H_3C)_2 Si(OTf)_2$ (prepared from diphenyldimethylsilane and triflic acid) with a base such as, for example, diisopropylethylamine and the like in a solvent such as, for example, dichloromethane and the like to form in situ a compound of Formula VI

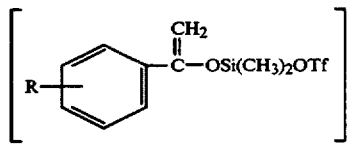

wherein R is as defined above which is subsequently reacted with 3-cyanobenzaldehyde to afford to compound of Formula VII

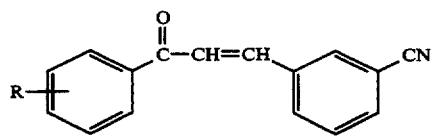

wherein R is as defined above. Treatment of a compound of Formula VII with a compound of Formula VI in the presence of $TrSnCl_5$ and a solvent such as, for example, dichloromethane and the like and subsequent treatment with tetrabutylammonium fluoride to afford a compound of Formula VIII

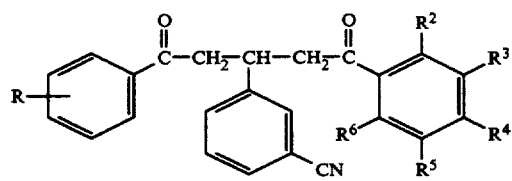

wherein R, $R^2$, $R^3$, $R^4$, $R^5$, and $R^6$ are as defined above. Treatment of a compound of Formula VIII with trimethylsilylazide and dibutyltin oxide in a solvent such as, for example, toluene affords a compound of Formula Ic.

A compound of Formula Id

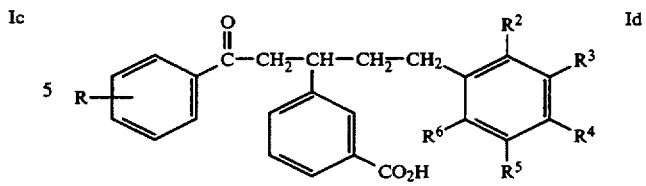

wherein R, $R^2$, $R^3$, $R^4$, $R^5$, and $R^6$ are as defined above; or a pharmaceutically acceptable base addition salt thereof is prepared by reacting a compound of Formula III and a compound of Formula IX

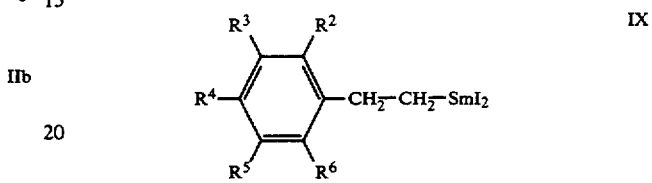

wherein $R^2$, $R^3$, $R^4$, $R^5$, and $R^6$ are as defined above in the presence of trimethylsilyl chloride and a catalytic amount of CuBr.DMS in a solvent such as, for example, diethyl ether and the like to afford a compound of Formula X

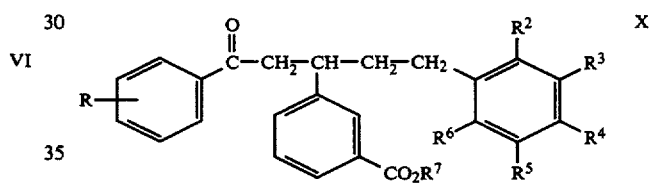

wherein R, $R^2$, $R^3$, $R^4$, $R^5$, $R^6$, and $R^7$ are as defined above. Treatment of a compound of Formula X with a base such as, for example, potassium trimethylsilanolate in a solvent such as, for example, diethyl ether and the like to afford a compound of Formula Id.

A compound of Formula Ie

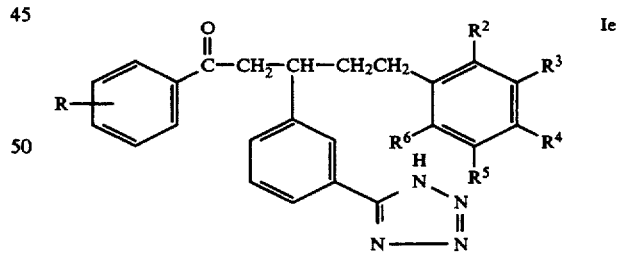

wherein R, $R^2$, $R^3$, $R^4$, $R^5$, and $R^6$ are as defined above; or a pharmaceutically acceptable base addition salt thereof is prepared by reacting a compound of Formula VII with a compound of Formula XI

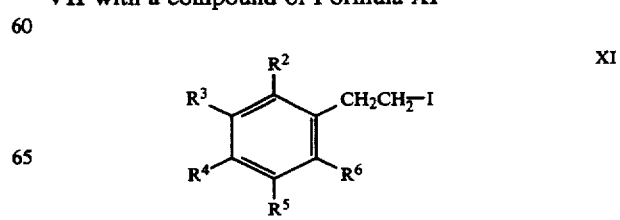

wherein $R^2$, $R^3$, $R^4$, $R^5$, and $R^6$ are as defined above with $SmI_2$ to afford a compound of Formula XII

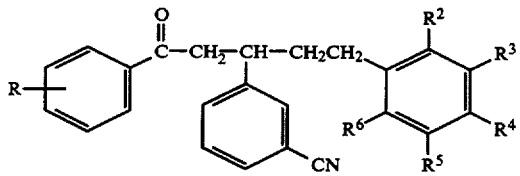

wherein R, $R^2$, $R^3$, $R^4$, $R^5$, and $R^6$ are as defined above Treatment of a compound of Formula XII with trimethylsilylazide and dibutyltin oxide to afford a compound of Formula Ie.

A compound of Formula IX is prepared from a compound of Formula XI

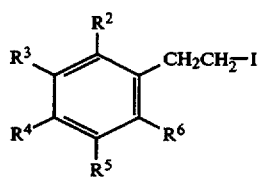

by reaction with $SmI_2$ in tetrahydrofuran and HMPA to afford a compound of Formula IX.

A compound of Formula XI is prepared from a compound of Formula XIII

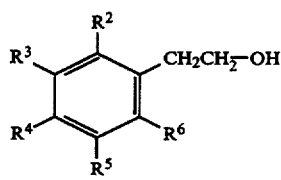

wherein $R^2$, $R^3$, $R^4$, $R^5$, and $R^6$ are as defined above by reaction with O-phenylene phosphorochloridite and pyridine in the presence of a solvent such as, for example, diethyl ether and the like to afford a compound of Formula X.

Compounds of Formula II, Formula IIa, Formula IIb, Formula IV, and Formula XIII are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% to 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low-melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low-melting wax, such as a mixture of fatty acid glycerides or cocoa butter, is first melted and the active component is dispersed homogeneously therein, as by stirring. The molten homogenous mixture is then poured into convenient-sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active compound in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antipsychotic agents, as agents to treat Parkinson's Disease or GI disorders, the compounds utilized in the pharmaceutical methods of this invention are administered at the initial dosage of about 0.01 mg to about 50 mg per kilogram daily. A daily dose range of about 0.01 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with small dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

3-[3-(4-Fluorophenyl)-1-[2-(4-fluorophenyl)2-oxoethyl]-3-oxopropyl]-benzoic acid A solution of 3-formylbenzoic acid (1 g, 6.66 mmol), 4'-fluoroacetophenone (1.21 g, 16 mmol), and sodium hydroxide (0.66 g, 16 mmol) in 60 mL of ethanol/water (1:1) is stirred at room temperature for 3 days. The reaction mixture is acidified with concentrated hydrochloric acid, and the resulting solid is collected by filtration. Recrystallization in hot chloroform provides 1.5 g of the title compound; mp 205°-207° C.

The following compound is prepared using methodology described in Example 1.

EXAMPLE 2

3-[3-(4-Chlorophenyl)-1-[2-(4-chlorophenyl)-2-oxoethyl]-3-oxopropyl]-benzoic acid; mp 183°-185° C.

EXAMPLE 3

3-[1-[2-(4-Chlorophenyl )-2-oxoethyl]-3-(2,5-dimethoxyphenyl)-3-oxopropyl]-benzoic acid Step A: Preparation of 3-[3-(2,5-Dimethoxyphenyl)-3-oxo-1-propenyl]-benzoic acid To a solution of 3-formylbenzoic acid (2.0 g, 13.3 mmol) and sodium hydroxide (1.32 g, 33 mmol) in 400 mL of ethanol/water (1:1) is added 2,5-dimethoxyacetophenone (2.4 g, 13.3 mmol) and the resulting solution is stirred overnight at room temperature. The mixture is acidified with concentrated hydrochloric acid and the resulting solid is collected by filtration after diluting the mixture with water (200 mL) to provide 2.9 g of the title compound; mp 152°-155° C.

Step B: Preparation of 3-[3-(2,5-Dimethoxyphenyl)-3-oxo-1-propenyl]-benzoic acid, methyl ester A solution of 3-[3-(2,5-dimethoxyphenyl)-3-oxo-1-propenyl]-benzoic acid (2.86 g, 9.15 mmol) in methanol (200 mL) is treated with sulfuric acid (0.5 mL) and heated under reflux for 6 hours. After standing at room temperature 12 hours, the resulting solid is collected by filtration and washed with methanol to provide 2.2 g of the title compound; mp 108°-110° C. Additional material (0.7 g) is obtained by concentrating the filtrate and washings under vacuum, partitioning the residue between saturated sodium bicarbonate solution and dichloromethane, and concentrating the dried (MgSO$_4$) organic layer to dryness.

Step C: Preparation of 3-[1-[2-(4-chlorophenyl)-2-oxoethyl]-3-(2,5-dimethoxyphenyl)-3-oxopropyl]-benzoic acid A solution of 3-[3-(2,5-dimethoxyphenyl)-3-oxo-1-propenyl ]-benzoic acid, methyl ester (2.0 g, 6.13 mmol) and TrSnCl$_5$ (0.2 g, 0.37 mmol) in dichloromethane (150 mL) is cooled to −78° C., treated with the 4-chloro[α-trimethylsiloxy]-styrene (2.63 g, 7.35 mmol), and stirred for 3 hours. After thin layer chromatography (TLC) indicates the disappearance of starting material, the reaction mixture is stirred 20 minutes with a saturated solution of sodium bicarbonate and the organic layer separated in a separatory funnel. The dried (MgSO$_4$) organic layer is concentrated to an oil under vacuum, dissolved in diethyl ether (400 mL), and treated with potassium trimethyl silanolate (3 g, 23.3 mmol). The mixture is stirred 3 days and the resulting solid is collected by filtration washing the cake thoroughly with diethyl ether. After drying, the solid is dissolved in water and treated with 1N hydrochloric acid. The resulting solid is collected by filtration, chromatographed over silica gel (SiO$_2$) using a medium pressure system eluting with 4% 2-propanol in dichloromethane. The pure fractions are combined and concentrated under vacuum to an oil. Trituration with diethyl ether (50 mL) provides 1.3 g of the title compound as a white solid; mp 164°-165° C.

The following compounds are prepared using methodology described in Example 3.

EXAMPLE 4

3-[1-[2-(4-Chlorophenyl )-2-oxoethyl]-3- (2,4-dimethoxyphenyl)-3-oxopropyl]-benzoic acid; mp 95°-99° C.

EXAMPLE 5

3-[1-[2-(4-Chlorophenyl)-2-oxoethyl]-3-(3-methoxyphenyl)-3-oxopropyl]-benzoic acid; mp 139°-140° C.

EXAMPLE 6

3-[1-[2-(4-Chlorophenyl)-2-oxoethyl]-3-(2-methoxyphenyl)-3-oxopropyl]-benzoic acid; mp 171°-172° C.

EXAMPLE 7

3-[1-[2-(4-Chlorophenyl)-2-oxoethyl]-3-(2,6-dimethoxyphenyl)-3-oxopropyl]-benzoic acid; mp 168°-169° C.

EXAMPLE 8

3-[1-[2-(4-Fluorophenyl)-2-oxoethyl]-3-(2-methoxyphenyl)-3-oxopropyl]-benzoic acid; mp 144°-145° C.

EXAMPLE 9

3-[3-(4,Fluorophenyl)-3-oxo-1-(2-oxo-2-phenylethyl )propyl]-benzoic acid; mp 155°-158° C.

EXAMPLE 10

3-[1-[2-(4-Fluorophenyl)-2-oxoethyl]-3-(4-methoxyphenyl)-3-oxopropyl]-benzoic acid; mp 154°-155° C.

EXAMPLE 11

3-[3-(2,5-Dimethoxyphenyl)-1-[2-(4-fluorophenyl)-2-oxoethyl]-3-oxopropyl]-benzoic acid; mp 138°-140° C.

EXAMPLE 12

3-[3-(2, 6-Dime thoxyphenyl)-1-[2-(4-f 1 uorophenyl)-2-oxoethyl]-3-oxopropyl]-benzoic acid; mp 110°-112° C.

EXAMPLE 13

3-[1-[2-(4-Chlorophenyl)-2-oxoethyl]-3-( 4-methoxyphenyl)-3-oxopropyl]-benzoic acid; mp 170°-171° C.

EXAMPLE 14

3-[1-[2-(4-Chlorophenyl)-2-oxoethyl]-3-(4-fluorophenyl)-3-oxopropyl]-benzoic acid; mp 191°-192° C.

EXAMPLE 15

3-[1-[2-(4-Fluorophenyl)-2-oxoethyl]-3-oxo-3-p-tolylpropyl]-benzoic acid; mp 176°-177° C.

EXAMPLE 16

3-[1-[2-(4-Chlorophenyl)-2-oxoethyl]-3-oxo-3-p-tolylpropyl]-benzoic acid; mp 158°-160° C.

EXAMPLE 17

1,5-Bis-(4-fluorophenyl)-3-[3-(1H-tetrazol-5-yl)-phenyl]-pentane-1,5-dione

Step A: Preparation of
3-[3-(4-Fluorophenyl)-3-oxo-1-propenyl]-benzonitrile

Triflic acid (3.2 g, 21 mmol) is added portionwise to diphenyldimethylsilane (2.22 g, 10.5 mmol) in 20 mL of dichloromethane and stirred for 1 hour. After cooling to −78° C., diisopropylethylamine (1.42 g, 11 mmol) and 4'-fluoroacetophenone (1.38 g, 10 mmol) are added and the reaction mixture stirred for another hour before adding 3-cyanobenzaldehyde (1.0 g, 7.62 mmol). After the reaction mixture is stirred 18 hours, it is diluted with 100 mL of dichloromethane and stirred 1 hour with a saturated solution of sodium bicarbonate. The organic layer is separated, dried (MgSO₄), concentrated and columned over SiO₂ eluting with dichloromethane to provide 0.8 g of the title compound; mp 170°-172° C.

Step B: Preparation of
3-[3-(4-Fluorophenyl)-1-[-2-(4-fluorophenyl)-2-oxoethyl]-3-oxopropyl]-benzonitrile 1-Fluoro-4-[1-[(trimethylsilyl) oxy]ethenyl]-benzene (0.98 g, 2.86 mmol) is added to a cooled (−78° C.) solution of 3-[3-(4-fluorophenyl)-3-oxo-1-propenyl]-benzonitrile (0.6 g, 2.39 mmol) and TrSnCl₅ (0.1 g, 0.19 mmol) in 70 mL of dichloromethane and stirred under nitrogen (N₂) for 3 hours. The reaction mixture is diluted with additional dichloromethane, washed with a saturated solution of sodium bicarbonate, dried (MgSO₄), and concentrated to an oil. The oil is taken up in 200 mL of diethyl ether and stirred with a few drops of tetrabutylammonium fluoride for 2 days. The diethyl ether is removed under vacuum and the residue columned over SiO₂ eluting with dichloromethane. Pure fractions are combined, concentrated, and triturated in diethyl ether-hexane to provide 0.9 g of analytical material; mp 120°-123° C.

Step C: Preparation of
1,5-Bis-(4-fluorophenyl)-3-[3-(1H-tetrazol-5-yl)phenyl]-pentane-1,5-dione A mixture of 3-[3-(4-fluorophenyl)-1-[2-(4-fluorophenyl)-2-oxoethyl]-3-oxopropyl]-benzonitrile (1 g, 2.1 mmol), trimethylsilylazide (0.48 g, 4.2 mmol), and dibutyltin oxide (0.05 g) is heated under N₂ in toluene (25 mL) at 100° C. for 18 hours. The toluene is removed under vacuum and the residue is dissolved in a small amount of methanol. The methanol is removed under vacuum and the residue chromatographed over SiO₂eluting with dichloromethane:2-propanol (4:1). Pure fractions are combined, concentrated, and triturated with diethyl ether to provide 0.8 g of the title compound; mp 162°-164C.

The following compound is prepared using methodology described in Example 17.

EXAMPLE 18

1,5-Bis-(4-chlorophenyl)-3- [3-(1H-tetrazol-5-yl)phenyl]-pentane-1, 5-dione; mp 198°-200° C.

EXAMPLE 19

3-[1-[2-(4-Chlorophenyl)ethyl]-3-oxo-3-phenylpropyl]-benzoic acid

Step A: Preparation of
3-(3-Oxo-3-phenyl-1-propenyl)-benzoic acid

A mixture of 3-formylbenzoic acid (2 g, 13.32 mmol), acetophenone (1.6 g, 13.32 mmol), and sodium hydroxide (1.06 g, 26.64 mmol) is stirred 18 hours in ethanol-water (175 mL, 1:1) and then acidified with concentrated hydrochloric acid. The resulting solid is collected by filtration and dried to provide 2.84 g of the title compound; mp 198°-201° C.

Step B: Preparation of
3-(3-Oxo-3-phenyl-1-propenyl)-benzoic acid, methyl ester

A slurry of 3-(3-oxo-3-phenyl-1-propenyl)-benzoic acid (2.84 g, 11.26 mmol) in methanol (150 mL) is treated with a few drops of sulfuric acid and heated under reflux for 8 hours. Upon cooling, a solid forms which is collected by filtration and washed thoroughly with methanol to provide 0.9 g of the title compound.

Step C: Preparation of
1-Chloro-4-(2-iodoethyl)-benzene

A solution of O-phenylene phosphorochloridite (10.12 g, 58 mmol) and pyridine (4.6 g, 58 mmol) in diethyl ether (200 mL) is cooled to 0° C. and treated dropwise with a solution of 4'-chlorophenethyl alcohol (9 g, 57.5 mmol) in diethyl ether (100 mL) and stirred 2 days. The resulting pyridine hydrochloride is collected by filtration and the filtrate is concentrated under vacuum to an oil. A solution of the oil in dichloromethane (150 mL) is stirred 10 days with iodine (14.72 g, 58 mmol) and then the reaction mixture is washed successively with 5% sodium hydroxide solution, 5% sodium bisulfite solution, and then saturated sodium chloride solution. The dried (MgSO₄) organic layer is concentrated in vacuo to provide 17.1 g of a pale yellow oil whose proton nuclear magnetic resonance (PMR) spectrum is consistent with its structure.

Step D: Preparation of 3-[1-[2-(4-Chlorophenyl)ethyl]-3-oxo-3-phenylpropyl]-benzoic acid, methyl ester A solution of SmI$_2$ (48 mL, 0.1N, 4.4 mmol) in tetrahydrofuran is treated with hexamethylphosphoramide (HMPA) (3.75 mL, 2.19 mmol) and stirred 5 minutes. A solution of 1-chloro-4- (2-iodoethyl) -benzene (0.6 g, 2.25 mmol) in tetrahydrofuran (5 mL) is added, stirred 10 minutes and cooled to −78° C. A catalytic amount of CuBr.DMS (45 rag, 0.225 mmol) is added to the reaction mixture which is stirred 5 minutes before a solution of 3-(3-oxo-3-phenyl-1-propenyl)-benzoic acid, methyl ester (0.4 g, 1.5 mmol) and trimethylsilyl chloride (0.75 mL, 5.58 mmol) in tetrahydrofuran (6 mL) is added. The reaction is stirred in the cold for 30 minutes, diluted with diethyl ether (400 mL), and filtered over a 2" cake of Al$_2$O$_3$. The ethereal solution is washed with water, dried (MgSO$_4$), and stirred with a few drops of tetrabutylammonium fluoride for 2 hours. The reaction mixture is concentrated and columned over SiO$_2$ eluting with dichloromethane to collect 0.5 g of an oil which is clean by PMR.

Step E: Preparation of 3-[1-[2-(4-Chlorophenyl)ethyl]-3-oxo-3-phenylpropyl]-benzoic acid 3-[1-(2-(4-Chlorophenyl)ethyl]-3-oxo-3-phenylpropyl]-benzoic acid, methyl ester (0.5 g, 1.22 mmol) is dissolved in diethyl ether (100 mL) and treated with potassium trimethylsilanolate (1 g, 7.8 mmol). After the mixture is stirred 18 hours, the resulting solid is collected by filtration and washed with diethyl ether. The dried cake is dissolved in water, acidified with 1N hydrochloric acid, and the resulting solid collected by filtration. Crystallization in diethyl ether-hexane provides 0.3 g of the title compound as large cottony needles; mp 93°-95° C.

The following compounds are prepared using methodology described in Example 19.

EXAMPLE 20

3-[3-(4-Chlorophenyl )-1-[2-(4-chlorophenyl)ethyl]-3-oxopropyl]-benzoic acid; amorphous solid

EXAMPLE 21

3-[1-[2-(4-Fluorophenyl)ethyl]-3-oxo-3-phenylpropyl]-benzoic acid; mp 100°-105° C.

EXAMPLE 22

3-[3-(4-Fluorophenyl)-1-[2-(4-fluorophenyl )ethyl]-3-oxopropyl]-benzoic acid; mp 113°-115° C.

EXAMPLE 23

3-[3-(4-Chlorophenyl)-3-oxo-1-[2-phenylethyl]-propyl]-benzoic acid; mp 116.6°-117.5° C.

We claim:

1. A compound of Formula I

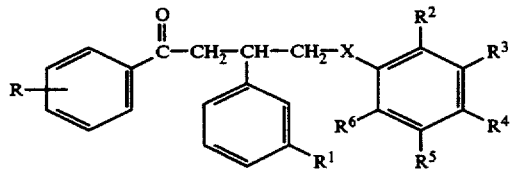

wherein X is

or —CH$_2$—;
R is hydrogen or halogen;
R$^1$ is —CO$_2$H or

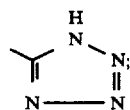

R$^2$, R$^3$, R$^4$, R$^5$, and R$^6$ are each the same or different and each is
hydrogen,
lower alkyl,
lower alkoxy, or
halogen;
or a pharmaceutically acceptable base addition salt thereof.

2. A compound according to claim 1 wherein R is
4-hydrogen or
4-halogen.

3. A compound according to claim 2 wherein R is
4-hydrogen,
4-chloro, or
4-fluoro.

4. A compound according to claim 3 selected from the group consisting of:
3-[3-(4- Fluorophenyl)- 1-[2-(4- fluorophenyl)-2-oxoethyl]-3-oxopropyl]-benzoic acid;
3-[3-(4-Chlorophenyl)-1-[2-(4-chlorophenyl )-2-oxoethyl]-3-oxopropyl]-benzoic acid;
3-[1-[2-(4-Chlorophenyl)-2-oxoethyl- 3-(2,5-dimethoxyphenyl)-3-oxopropyl]-benzoic acid;
3-[1-[2-(4-Chlorophenyl)-2-oxoethyl]-3- (2,4-dimethoxyphenyl)-3-oxopropyl]-benzoic acid;
3-[1-[2-(4-Chlorophenyl)-2-oxoethyl]-3-( 3-methoxyphenyl)- 3-oxopropyl]-benzoic acid;
3-[1-[2-(4-Chlorophenyl)-2-oxoethyl]-3-(2-methoxyphenyl)-3-oxopropyl]-benzoic acid;
3-[1-[2-(4-Chlorophenyl)-2-oxoethyl]-3- (2,6-dimethoxyphenyl) -3-oxopropyl]-benzoic acid;
3-[1-[2-(4-Fluorophenyl -2-oxoethyl]-3- (2-methoxyphenyl)-3-oxopropyl]-benzoic acid;
3-[3-(4-Fluorophenyl)-3-oxo-1-(2-oxo-2-phenylethyl)propyl]-benzoic acid;
3-[1-[2-(4-Fluorophenyl)-2-oxoethyl]-3-(4-methoxyphenyl)-3-oxopropyl]-benzoic acid;
3-[3-(2,5-Dimethoxyphenyl)-1-[2-(4-fluorophenyl)-2-oxoethyl]-3-oxopropyl]-benzoic acid;
3-[3-(2, 6-Dimethoxyphenyl )-1-[2-(4-fluorophenyl)-2-oxoethyl]-3-oxopropyl]-benzoic acid;
3-[1-[2-(4-Chlorophenyl)-2-oxoethyl]-3-(4-methoxyphenyl)-3-oxopropyl]-benzoic acid;
3-[1-[2-(4-Chlorophenyl)-2-oxoethyl]-3-(4-fluorophenyl)-3-oxopropyl]-benzoic acid;
3-[1-[2-(4-Fluorophenyl)-2-oxoethyl]-3-oxo-3-p-tolylpropyl]-benzoic acid;
3-[1-[2-(4-Chlorophenyl) -2-oxoethyl]-3-oxo3-p-tolylpropyl]-benzoic acid;
1,5-Bis-(4-fluorophenyl)-3-[3-(1H-tetrazol-5-yl )phenyl]-pentane-1,5-dione;
1,5-Bis-(4-chlorophenyl-3-[3-(1H-tetrazol-5-yl ) phenyl]-pentane-1,5-dione;

3-[1-[2-(4-Chlorophenyl)ethyl]-3-oxo-3-phenyl-propyl]-benzoic acid;

3-[3-(4-Chlorophenyl)-1-[2-(4-chlorophenyl)ethyl]-3-oxopropyl]-benzoic acid;

3-[1-[2-(4-Fluorophenyl)ethyl]-3-oxo-3-phenyl-propyl]-benzoic acid;

3-[3-(4-Fluorophenyl)-1-[2-(4-fluorophenyl)ethyl]-3-oxopropyl]-benzoic acid; and 3-[3-(4-Chlorophenyl)-3-oxo-1-[2-phenylethyl]-propyl]-benzoic acid.

5. A method of treating schizophrenia comprising administering to a host suffering therefrom a therapeutic effective amount of a compound according to claim 1 in unit dosage form.

6. A pharmaceutical composition adapted for administration as an agent for treating schizophrenia, Parkinson's disease, or gastrointestinal disorders comprising a therapeutic effective amount of a compound according to claim 1 in admixture with a pharmaceutically acceptable excipient, diluent, or carrier.

* * * * *